United States Patent
Keady et al.

(10) Patent No.: US 8,251,925 B2
(45) Date of Patent: Aug. 28, 2012

(54) DEVICE AND METHOD FOR RADIAL PRESSURE DETERMINATION

(75) Inventors: John P. Keady, Boca Raton, FL (US); Wayne Staab, Dammeron Valley, UT (US)

(73) Assignee: Personics Holdings Inc., Boca Raton, FL (US)

(*) Notice: Subject to any disclaimer, the term of this patent is extended or adjusted under 35 U.S.C. 154(b) by 0 days.

(21) Appl. No.: 12/347,655

(22) Filed: Dec. 31, 2008

(65) Prior Publication Data

US 2009/0192407 A1 Jul. 30, 2009

Related U.S. Application Data

(60) Provisional application No. 61/018,444, filed on Dec. 31, 2007.

(51) Int. Cl.
 *A61B 5/103* (2006.01)
 *A61B 5/117* (2006.01)
(52) U.S. Cl. ...................................................... 600/587
(58) Field of Classification Search .................. 600/587, 600/559, 560, 561; 181/129–135; 381/328, 381/60; 73/585; 128/864–865
See application file for complete search history.

(56) References Cited

U.S. PATENT DOCUMENTS

| | | | | |
|---|---|---|---|---|
| 2,535,258 A | | 12/1950 | Bland | |
| 3,312,222 A | * | 4/1967 | Dwyer | 606/121 |
| 3,505,999 A | * | 4/1970 | Harvey et al. | 128/865 |
| 3,602,654 A | | 8/1971 | Victoreen | |
| 3,882,848 A | * | 5/1975 | Klar et al. | 600/559 |
| 4,057,051 A | * | 11/1977 | Kerouac | 600/559 |
| 4,079,198 A | * | 3/1978 | Bennett | 600/559 |
| 4,237,905 A | * | 12/1980 | Keller et al. | 600/559 |
| 4,641,661 A | * | 2/1987 | Kalarickal | 600/557 |
| 4,712,566 A | * | 12/1987 | Hok | 600/561 |
| 4,741,344 A | | 5/1988 | Danby et al. | |
| 4,834,211 A | | 5/1989 | Bibby et al. | |
| 4,896,679 A | | 1/1990 | St. Pierre | |
| 4,913,165 A | * | 4/1990 | Fishgoyt | 128/865 |
| 4,962,537 A | | 10/1990 | Basel et al. | |
| 5,333,622 A | | 8/1994 | Casali et al. | |
| 5,483,027 A | | 1/1996 | Krause | |
| 5,533,514 A | * | 7/1996 | Lavigne et al. | 600/557 |
| 5,984,879 A | * | 11/1999 | Wallace et al. | 600/587 |
| 6,094,494 A | | 7/2000 | Haroldson | |

(Continued)

FOREIGN PATENT DOCUMENTS

WO   WO 2007004083   *   1/2007

OTHER PUBLICATIONS

Lubrizol Thermedics™ Pellethane® 2363-80A Polyurethane Elastomer, Ether Based, http://www.matweb.com/search/datasheet ; Date: 2009.

*Primary Examiner* — Max Hindenburg
*Assistant Examiner* — H. Q. Nguyen
(74) *Attorney, Agent, or Firm* — RatnerPrestia

(57) ABSTRACT

Methods and apparatus for measuring ear canal wall pressure comfort level are provided. An expandable pressure exertion device is inserted into an orifice. The device is expanded inside the orifice in increments of pressure. A threshold level is saved where a user indicates that the pressure exerted against the walls of the orifice is becoming at least one of uncomfortable, painful, and noticeable.

8 Claims, 3 Drawing Sheets

U.S. PATENT DOCUMENTS

| | | |
|---|---|---|
| 6,256,396 B1 | 7/2001 | Cushman |
| 6,339,648 B1 | 1/2002 | McIntosh et al. |
| 6,393,130 B1 | 5/2002 | Stonikas et al. |
| 6,648,873 B2 * | 11/2003 | Arenberg et al. ............. 604/509 |
| 6,671,381 B1 | 12/2003 | Lux-Wellenhof |
| 7,130,437 B2 | 10/2006 | Stonikas et al. |
| 7,164,775 B2 | 1/2007 | Meyer et al. |
| 7,227,968 B2 | 6/2007 | van Halteren et al. |
| 7,362,875 B2 | 4/2008 | Saxton et al. |
| 7,387,187 B2 | 6/2008 | Widmer et al. |
| 7,604,605 B2 * | 10/2009 | Zvuloni ........................ 600/587 |
| 8,047,207 B2 * | 11/2011 | Perez et al. .................. 128/864 |
| 2004/0097839 A1 * | 5/2004 | Epley ............................ 600/595 |
| 2006/0159298 A1 | 7/2006 | von Dombrowski et al. |
| 2007/0045092 A1 * | 3/2007 | Voto et al. ..................... 200/181 |
| 2007/0116319 A1 | 5/2007 | Hagberg |
| 2007/0156068 A1 * | 7/2007 | Dubey et al. .................. 600/588 |
| 2008/0144871 A1 | 6/2008 | Purcell et al. |
| 2009/0071486 A1 * | 3/2009 | Perez et al. ................... 128/858 |
| 2009/0116677 A1 * | 5/2009 | Jones et al. .................... 381/380 |
| 2009/0173353 A1 | 7/2009 | Purcell et al. |
| 2009/0320858 A1 | 12/2009 | Purcell et al. |
| 2009/0320859 A1 | 12/2009 | Purcell et al. |

* cited by examiner

DEVICE AND METHOD FOR RADIAL PRESSURE DETERMINATION

CROSS-REFERENCE TO RELATED APPLICATIONS

This application claims the benefit of U.S. provisional patent application No. 61/018,444 filed 31 Dec. 2007. The disclosure of which is incorporated herein by reference in its entirety.

FIELD OF THE INVENTION

The present invention relates to devices and methods for pressure measurements in ear canals.

BACKGROUND OF THE INVENTION

Various devices (e.g. headphones, earbuds, behind the ear, hearing aids, and other devices that direct acoustic energy into an acoustic measuring device (e.g., ear)) have been designed for various uses. Many conventional systems have difficulty sealing in the ear canal. Other orifice (e.g., ear. mouth, anus, nose, artery, vein, pipe, indentation) insertion devices have additionally have sealing issues. Various methods of sealing can impact the orifice walls. The amount of impact is important for designing comfortable orifice sealing devices.

SUMMARY OF THE INVENTION

At least one exemplary embodiment is directed to a method of measuring ear canal wall pressure comfort level comprising: inserting an expandable pressure exertion device into an orifice; expanding the device inside the orifice in increments of pressure; and saving a threshold level where a user indicates that the pressure exerted against the walls of the orifice is becoming at least one of uncomfortable, painful, and noticeable.

BRIEF DESCRIPTION OF THE DRAWINGS

Exemplary embodiments of present invention will become more fully understood from the detailed description and the accompanying drawings, wherein.

DETAILED DESCRIPTION OF EXEMPLARY EMBODIMENTS OF THE PRESENT INVENTION

Figure 1:
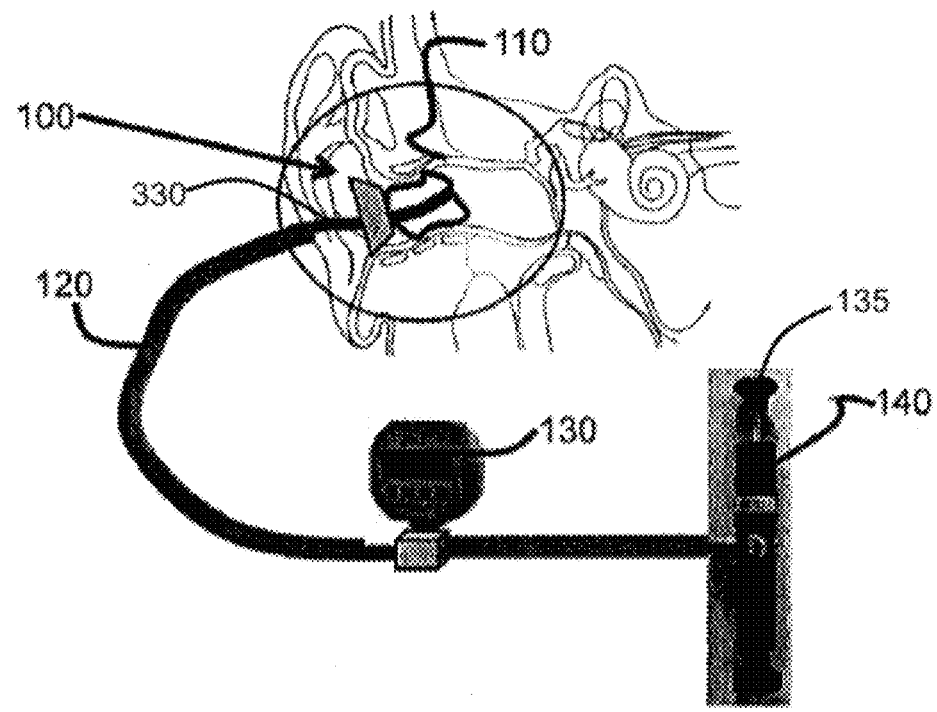
FIG. 1 illustrates an experimental setup for measuring orifice radial pressures in accordance with at least one exemplary embodiment.

The following description of exemplary embodiment(s) is merely illustrative in nature and is in no way intended to limit the invention, its application, or uses.

Exemplary embodiments are directed to or can be operatively used on various wired or wireless devices (e.g., earbuds, headphones, ear terminal, behind the ear devices or other acoustic devices as known by one of ordinary skill, and equivalents) or other devices that can be part of a user interface or inserted into an orifice (e.g., ear canal, nose, artery, vein, cavity, recess, anus, throat, pipe, chamber).

Processes, techniques, apparatus, and materials as known by one of ordinary skill in the art may not be discussed in detail but are intended to be part of the enabling description where appropriate. For example specific materials may not be listed for achieving each of the targeted properties discussed, however one of ordinary skill would be able, without undo experimentation, to determine the materials needed given the enabling disclosure herein.

Additionally exemplary embodiments are not limited to ear devices, for example some functionality can be implemented on other systems with speakers and/or microphones for example computer systems, PDAs, Blackberry® smartphones, cell and mobile phones, and any other device that emits or measures acoustic energy but also for common items such as cups, utensils, medical inserts and devices, and pipe inserts. Additionally, exemplary embodiments can be used with digital and non-digital acoustic systems. Additionally various receivers and microphones can be used, for example MEMs transducers, diaphragm transducers, for example Knowle's FG and EG series transducers.

Notice that similar reference numerals and letters refer to similar items in the following figures, and thus once an item is defined in one figure, it may not be discussed or further defined in the following figures.

Exemplary Embodiments

Note that many of the sizes of the devices can vary so that an device is about 10 s of mm in diameters, and 10 s mm in length, with a mass varying from 5 grams to hundreds of grams. For example sealing sections can be in the minimal compressed dimension roughly 7 mm (ring diameter), whereas in the uncompressed dimension can be 14 mm (ring diameter). For example at least one exemplary embodiment has a non deformable core diameter of about 5 mm with a length of about 25 mm, with an additional surrounding deformable lay (e.g., sealing section) of an additional 5 mm on either side of the core. The instrument package can be roughly a cylinder of length 10 mm and diameter of about 14 mm.

Note that some of the materials in the device (e.g., outer coating) can be a membrane or multiple membranes and/or layer configuration in accordance with at least one exemplary embodiment. In one configuration an outer membrane contains a fillable material, such as viscosity variable polymers (e.g., that gellify when reaching body temperature) while underneath another membrane encapsulates another medium, which can be a fluid (e.g., liquid, gas) that can be increased or reduced to inflate the inner membrane in the positive/negative radial direction. The medium can be fed via an inflation tube. The device can also include an acoustic channel. Note that although two membranes are mentioned, more can be used with various levels of inflation and various materials, or not inflated and expanded based on temperature or other energy variation methods.

The device can include a sealing section, that can be made of various materials, for example viscosity variable polymers. As the device is inserted into an orifice (e.g., ear, mouth, anus, nose, artery, vein) a resistance force can be encountered by a portion of the sealing section. The force can act as an energy variation event which can change the physical properties, for example liquefies (e.g., lowers the viscosity, could still be gel like) the fillable material allowing easy flow or deforms a deformable sealing section. As the impulse forces stop and stability sets in (net equilibrium force reduced) the portion of the sealing section that liquefied in response to a force gellifies seating the device 1300.

Note that in some materials there is a phase shift in the temporal response of the medium. For example when a force is applied there may be a 10 msec delay in the liquefaction (change in viscosity) of the sealing element's fillable material.

FIG. 1 illustrates an experimental setup for measuring orifice radial pressures in accordance with at least one exemplary embodiment. An expandable pressure exertion device 100, can be inserted into an orifice 110. The pressure exertion device can be fed via a pressure tube 120, where the pressure can be monitored 130 (e.g., AccuGauge AG100), and the pressure can be changed via a pressure generation system 140 (e.g., SCANDURA BA-12).

Figure 2:
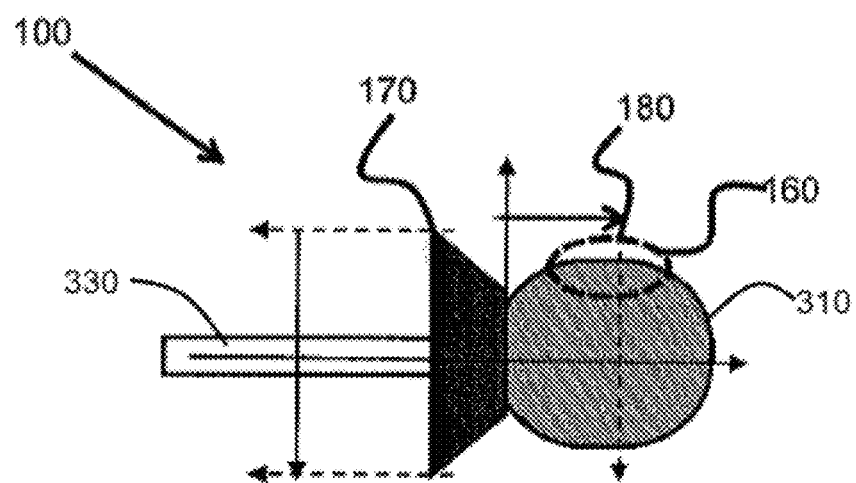
FIG. 2 illustrates an expandable pressure exertion device in accordance with at least one exemplary embodiment.

FIG. 2 illustrates an expandable pressure exertion device 100 in accordance with at least one exemplary embodiment. A reference element 170 can be used to provide a reference location from the distance (e.g., 180) which pressure exertions (e.g., region 160) against the orifice wall can be measured. FIG. 2 illustrates an expandable pressure exertion device 100 comprising: a stent 330, a reference element 170, and a balloon 310.

Figure 3:
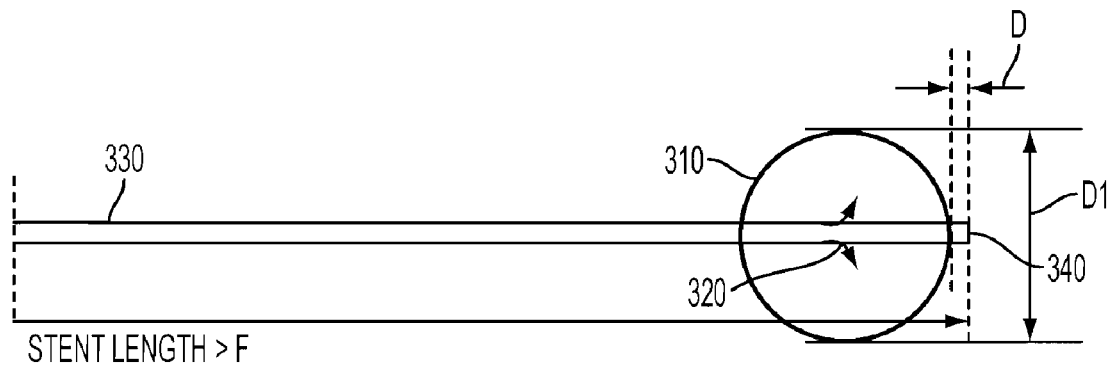
FIG. 3 illustrates an expandable pressure exertion device in accordance with at least one exemplary embodiment.

FIG. 3 illustrates an expandable pressure exertion device in accordance with at least one exemplary embodiment. The pressure exertion device can include a stent 330 (e.g., Pellethane SSD, Part No. 115-0177), a membrane 310 (e.g., a balloon, Low Durometer, Part No. 10000000BB), with feed holes 320 to increase the pressure within the membrane 310. Note that membrane 310 can be elastic or non elastic or a combination. The end of the stent 330 can be sealed 340.

Figure 4:
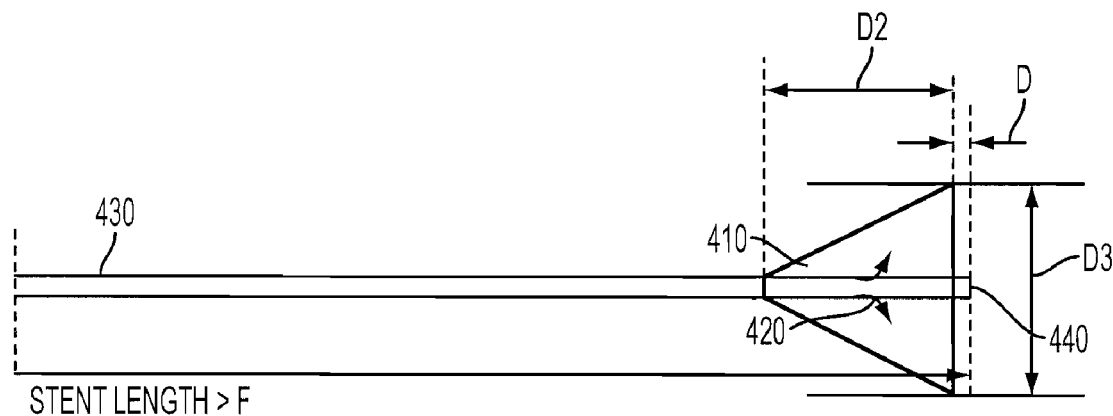
FIG. 4 illustrates an expandable pressure exertion device in accordance with at least one exemplary embodiment.

FIG. 4 illustrates an expandable pressure exertion device in accordance with at least one exemplary embodiment. The pressure exertion device can include a stent 430 (e.g., Pellethane SSD, Part No. 115-0177), a membrane 410 (e.g., a conical balloon, Low Durometer), with feed holes 420 to increase the pressure within the membrane 310. Note that membrane 410 can be elastic or non elastic or a combination. The end of the stent 430 can be sealed 440.

Figure 5:
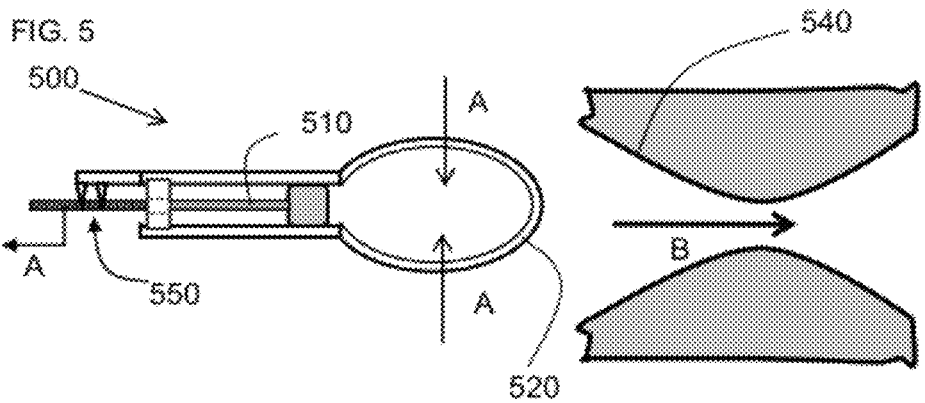
FIG. 5 illustrates an expandable pressure exertion device in accordance with at least one exemplary embodiment.

FIG. 5 illustrates an expandable pressure exertion device 500 in accordance with at least one exemplary embodiment, which can be inserted B into an orifice 540. The device 500 when inserted B can have a membrane 520 (e.g., which can be elastic or non elastic or some combination), which when depressed A, can move a piston shaft 510, and read from a marker 550. The depressed membrane A can be related to pressure exerted on a wall of a orifice.

Figure 6:
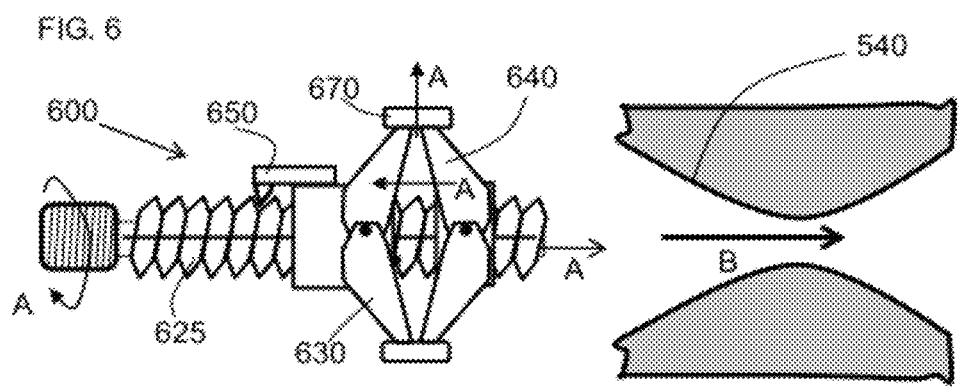
FIG. 6 illustrates an expandable pressure exertion device in accordance with at least one exemplary embodiment.

FIG. 6 illustrates an expandable pressure exertion device 600 (e.g., expandable clip) in accordance with at least one exemplary embodiment, which can be inserted B into an orifice 540. The device 600 when inserted B can have a pad 670. As a rotation mechanism 650 (e.g., a screw 625) is rotated A, the pads 670 can move in a direction A exerting a pressure on the wall of the orifice. For example as the screw 625 rotates, the screw 625 can translate through a stability element 630 which can pivot about a point. The translation of the screw 625 can translate a movement element 640, which is operatively attached to pad(s) 670. Thus as the screw 625 translates the pad(s) 670 can move exerting a force A, which can be related to a pressure exerted by knowing the area of the pads 670.

Figure 7:
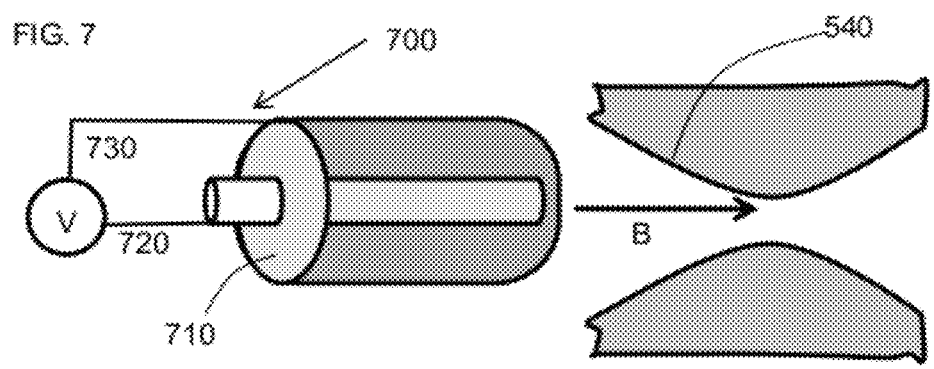
FIG. 7 illustrates an expandable pressure exertion device in accordance with at least one exemplary embodiment.

FIG. 7 illustrates an expandable pressure exertion device 700 in accordance with at least one exemplary embodiment, which can be inserted B into an orifice 540. For example an electroactive gel 710 can be expanded by applying a voltage across electrodes attached to lead wires 730 and 720.

At least one exemplary embodiment is directed to a method of measuring ear canal wall pressure comfort level comprising: inserting an expandable pressure exertion device into an orifice; expanding the device inside the orifice in increments of pressure; and saving a threshold level where a user indicates that the pressure exerted against the walls of the orifice is becoming at least one of uncomfortable, painful, and noticeable. For example when the device is inserted into the orifice, gradually the pressure can be increased until a user indicates whether the pressure is uncomfortable for a designated period of time or usage (e.g., jogging). Note that any membrane containing expandable pressure exertion device can have the pressure increased by adding more fluid (e.g., gas or liquid).

In at least one exemplary embodiment the reference element 170 can be a flange that is designed to stop at the aperture of an orifice (stop flange).

Note that although a device is described herein, other devices that can use various viscosity polymers or sealing elements are also meant to fall within the scope of at least one exemplary embodiment of the present invention, for example a drain plug, a pipe plug, a device for sealing the pipe up to a design pressure at which the gel will liquefy and be released or other sealing or impact type situations.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions of the relevant exemplary embodiments. For example, if words such as "orthogonal", "perpendicular" are used the intended meaning is "substantially orthogonal" and "substantially perpendicular" respectively. Additionally although specific numbers may be quoted in the claims, it is intended that a number close to the one stated is also within the intended scope, i.e. any stated number (e.g., 20 mils) should be interpreted to be "about" the value of the stated number (e.g., about 20 mils).

Thus, the description of the invention is merely exemplary in nature and, thus, variations that do not depart from the gist of the invention are intended to be within the scope of the exemplary embodiments of the present invention. Such variations are not to be regarded as a departure from the spirit and scope of the present invention.

What is claimed is:

1. A method of measuring a threshold pressure level of an expandable pressure exertion device against an ear canal wall comprising:

inserting the expandable pressure exertion device into an ear canal of a user;

repeatedly expanding the expandable pressure exertion device inside the ear canal in increments of increasing pressure and storing each increment of increasing pressure, each increment of increasing pressure by the expandable pressure exertion device exerting more force on the ear canal wall;

receiving an indication from the user that the force on the ear canal wall associated with one of the increments of increasing pressure is at least at a predetermined pressure level for a predetermined period of time; and responsive to the indication, saving the one of the increments of increasing pressure as the threshold pressure level.

2. The method according to claim 1, where the expandable pressure exertion device is an expandable balloon, and the expanding of the expandable pressure exertion device includes increasing an amount of a fluid in the expandable balloon.

3. The method according to claim 2, where the fluid is a gas.

4. The method according to claim 1, where the expandable pressure exertion device is an electroactive polymer, and the expanding of the expandable pressure exertion device includes applying at least one of a voltage or a current across at least one portion of the electroactive polymer.

5. The method according to claim 1, where the expandable pressure exertion device is an expandable clip, and the expanding of the expandable pressure exertion device includes turning a screw mechanism of the expandable clip to expand at least two pads attached to the expandable clip.

6. The method according to claim 1, where the expandable pressure exertion device is an insertable device, and the expanding of the expandable pressure exertion device includes depressing a membrane of the insertable device, where an amount of depression is related to a pressure value corresponding to the increments of increasing pressure.

7. The method according to claim 1, where the expandable pressure exertion device has a reference element, the method including establishing a reference point by the reference element from which a location along the ear canal wall at which the expandable pressure exertion device exerts the force is measured.

8. The method according to claim 2, where the expandable balloon is attached to a stent, and where the stent has an inflation hole through which the fluid enters the balloon.

* * * * *